US008540758B2

(12) United States Patent
Nanavati

(10) Patent No.: US 8,540,758 B2
(45) Date of Patent: Sep. 24, 2013

(54) BIFURCATION STENT AND DELIVERY SYSTEM

(76) Inventor: Vimal I. Nanavati, Chula Vista, CA (US)

(*) Notice: Subject to any disclaimer, the term of this patent is extended or adjusted under 35 U.S.C. 154(b) by 973 days.

(21) Appl. No.: 11/945,967

(22) Filed: Nov. 27, 2007

(65) Prior Publication Data

US 2009/0182270 A1    Jul. 16, 2009

(51) Int. Cl.
*A61F 2/06* (2013.01)

(52) U.S. Cl.
USPC ......................................... 623/1.11

(58) Field of Classification Search
USPC ........ 623/1.11, 1.35, 1.12, 1.15; 604/100.01, 604/101.03, 103.1; 606/192, 194
See application file for complete search history.

(56) References Cited

U.S. PATENT DOCUMENTS

| 4,896,670 | A | 1/1990 | Crittenden |
| 5,797,878 | A | 8/1998 | Bleam |
| 6,113,613 | A | 9/2000 | Spaulding |
| 6,325,826 | B1 * | 12/2001 | Vardi et al. .................. 623/1.35 |
| 6,395,018 | B1 * | 5/2002 | Castaneda .................. 623/1.13 |
| 7,252,679 | B2 | 8/2007 | Fischell |
| 2003/0028233 | A1 * | 2/2003 | Vardi et al. .................. 623/1.11 |
| 2004/0138732 | A1 * | 7/2004 | Suhr et al. .................. 623/1.11 |
| 2005/0131517 | A1 * | 6/2005 | Hartley et al. ............... 623/1.13 |

* cited by examiner

*Primary Examiner* — Thomas McEvoy
(74) *Attorney, Agent, or Firm* — Sheppard Mullin Richter & Hampton LLP

(57) ABSTRACT

The present invention is directed to a device comprising a catheter tube, which includes a round opening and two platinum radio-opaque markers on its distal end; a guide-wire; a balloon, which includes a wedge-shaped opening; and a stent, which includes an elliptical-shaped opening and three platinum radio-opaque markers. The invention is also directed to methods for using the device for deploying stents to treat bifurcation lesions.

7 Claims, 4 Drawing Sheets

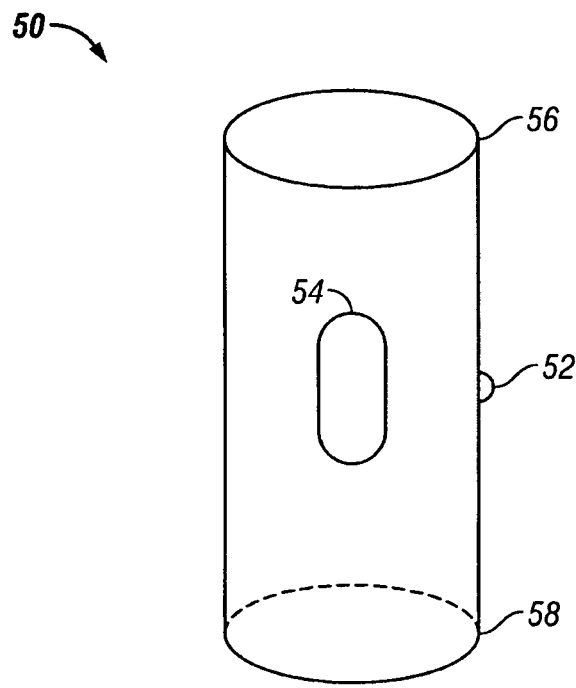
FIG. 2A
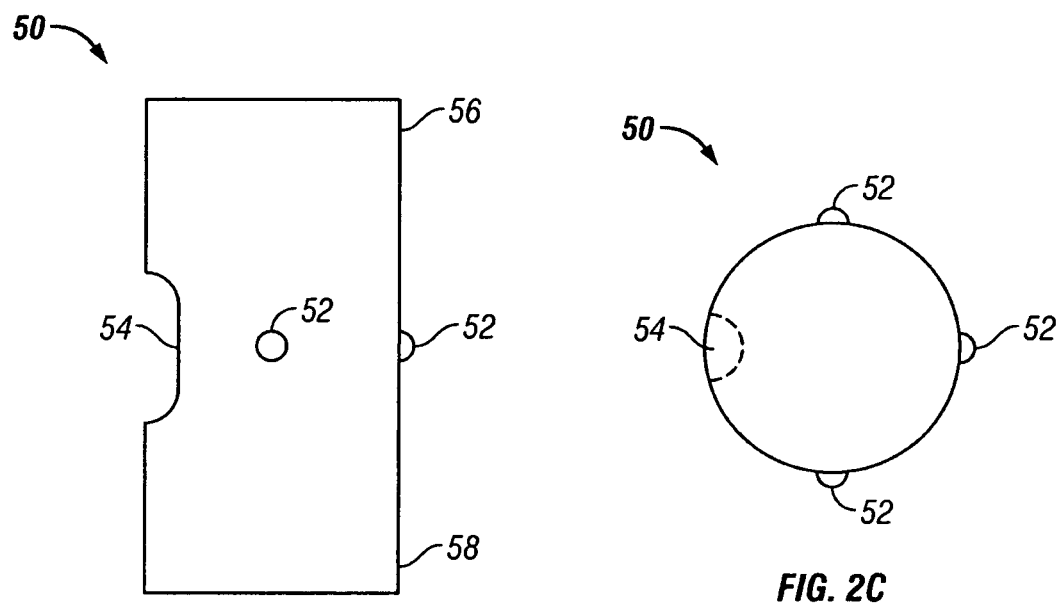
FIG. 2B
FIG. 2C

BIFURCATION STENT AND DELIVERY SYSTEM

FIELD OF THE INVENTION

The present invention relates generally to medical devices and medical methods. More particularly, the present invention relates to devices and methods useful for deploying stents to treat bifurcation lesions.

BACKGROUND OF THE INVENTION

Atherosclerosis is the progressive narrowing and hardening of arteries over time. The process is characterized by plaque buildup on the inside of the arteries. Atherosclerosis is known to occur to some degree with aging, but other risk factors that accelerate this process have been identified, including high cholesterol, high blood pressure, smoking, diabetes and a family history for atherosclerotic disease.

Percutaneous transluminal coronary angioplasty is a common procedure used by doctors to treat atherosclerosis. The procedure involves mechanically dilating a narrowed or totally-obstructed artery by passing a balloon catheter through the artery to the area of plaque buildup and inflating the balloon, which compresses the plaque and increases the interior diameter of the artery. Doctors generally use a guide-wire across the arterial blockage to advance the balloon catheter to the site of the blockage.

During angioplasty, doctors may also place a stent in the newly widened artery to hold up the artery and decrease the risk of restenosis or re-narrowing of the artery. Stent installation generally follows the same angioplasty procedure, except the balloon is attached to a stent and together they are positioned at the site of blockage using a guide-wire. The balloon is then inflated to push the stent against the artery wall, which anchors the stent in place. The balloon is then deflated and removed along with the catheter and the guide-wire.

Although the use of a stent during angioplasty is generally preferred, doctors have found it difficult, if not impossible, to safely and effectively deploy the stent in bifurcated arteries—arteries divided into two equally important branches or, alternatively, a main artery branch giving away to a side branch. Specifically, inflating the balloon and pushing the stent against the artery wall in one branch may force plaque into the other branch of the artery, effectively blocking that branch, which could cause a heart attack if the artery supplies blood to the heart or a stroke if the artery supplies blood to the brain.

Alternatively, doctors have tried to use two guide-wires (one in each arterial branch) so that a balloon can be advanced to each branch and inflated either substantially simultaneously or in closely spaced intervals. In the event a stent is advanced into a bifurcation lesion after both branches have been dilated, the guide-wire not used for placement of the stent must be removed because the guide-wire would become permanently trapped in the arterial wall when the stent is deployed. Additionally, if the second guide-wire, which was not used for stenting, is removed and the stent is deployed using the first guide wire, some of the plaque residue can be squeezed into the side branch creating a blockage.

SUMMARY OF THE INVENTION

The present invention provides devices for treating bifurcation lesions. In one embodiment, the device comprises a substantially cylindrical housing sized to fit in the internal volume of an artery, an opening in the housing between the proximal and distal ends of the housing, and at least one metal radio-opaque marker on the housing. The opening in the housing can accommodate the passage of a standard balloon catheter. The device preferably includes three metal radio-opaque markers on the housing, which are spaced at approximately 90 degree angles relative to the opening in the housing and which are used to identify the location of the device for alignment with an arterial branch. The metal radio-opaque markers may be gold, platinum or any other suitable metal.

In some embodiments, the device includes a balloon, which may be attached to the housing. The balloon includes an opening that may be substantially equidistant from the proximal and distal ends of the balloon. Preferably, the opening in the balloon is wedge-shaped.

Some embodiments of the device further include a catheter tube with an opening located near the catheter's distal end. The catheter tube includes at least one metal radio-opaque marker located substantially near the opening of the catheter tube, and preferably includes two metal radio-opaque markers on opposite sides of the opening. The metal radio-opaque markers on the catheter tube identify the position of the opening relative to the opening of an arterial branch which, when the openings in the housing, the balloon and the catheter tube are aligned, allows passage of a guide-wire through the openings and into an arterial branch.

The present invention also provides methods for deploying stents to treat bifurcation lesions. In one embodiment, the method comprises the steps of accessing the internal volume of an artery, which is divided into a first and second branch; inserting a balloon catheter, which comprises a first catheter tube, a first balloon and a first stent, into the internal volume; using a first guide-wire to advance the balloon catheter to a site of plaque buildup substantially near the two branches; positioning the balloon catheter substantially at the center of the plaque buildup in a first branch; advancing a second guide-wire through the first catheter tube to a position substantially near the center of the first balloon; using at least one metal radio-opaque marker on the balloon catheter as a guide to align openings in the first catheter tube, the first balloon and the first stent, respectively, with an opening to the second branch; advancing the second guide-wire into the second branch through the openings in the first catheter tube, first balloon and first stent; inflating the first balloon to deploy the first stent; deflating the first balloon; advancing a third guide-wire into the second branch and withdrawing the first balloon and first catheter tube and the first and second guide-wires; using the third-guide wire to advance a second balloon catheter, which comprises a second catheter tube, a second balloon and a second stent, to the second branch through the first stent; advancing a fourth guide-wire into the first branch; using the fourth guide-wire to advance a third balloon catheter, which comprises a third catheter tube and a third balloon, to the site of the previously deployed first stent in the first branch; inflating the second and the third balloons, whereby the second stent is deployed in the second branch; and deflating the second and third balloons and removing them from the internal volume. In another embodiment, the method comprises the steps of accessing the internal volume of an artery, which is divided into a first and second branch; inserting a balloon catheter, which comprises a first catheter tube, a first balloon and a first stent, into the internal volume; using a first guide-wire to advance the balloon catheter to a site of plaque buildup substantially near the two branches; positioning the balloon catheter substantially at the center of the plaque buildup in a first branch; advancing a second guide-wire through the first catheter tube to a position substantially near the center of the first balloon; using at least one metal radio-opaque marker on the balloon catheter as a guide to align openings in the first catheter tube, the first balloon and the first stent, respectively, with an opening to the second branch; advancing the second guide-wire into the second branch through the openings in the first catheter tube, first balloon and first stent; inflating the first balloon to deploy the first stent; deflating the first balloon and withdrawing the first balloon and first catheter tube while leaving the first and second guide-wires in the first and second branches; advancing a second balloon catheter, which comprises a second catheter tube, a second balloon and a second stent, to the second branch through the first stent; advancing a third balloon catheter, which comprises a third catheter tube and a third balloon, to the site of the previously deployed first stent in the first branch; inflating the second and the third balloons, whereby the second stent is deployed in the second branch; and deflating the second and third balloons and removing them from the internal volume.

BRIEF DESCRIPTION OF THE DRAWINGS

FIG. 2A is a side view of an embodiment of a stent device according to the present invention.

FIG. 2B is another side view of an embodiment of a stent device according to the present invention.

FIG. 2C is a top view of an embodiment of a stent device according to the present invention.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

A. Devices of the Present Invention

Figure 1:
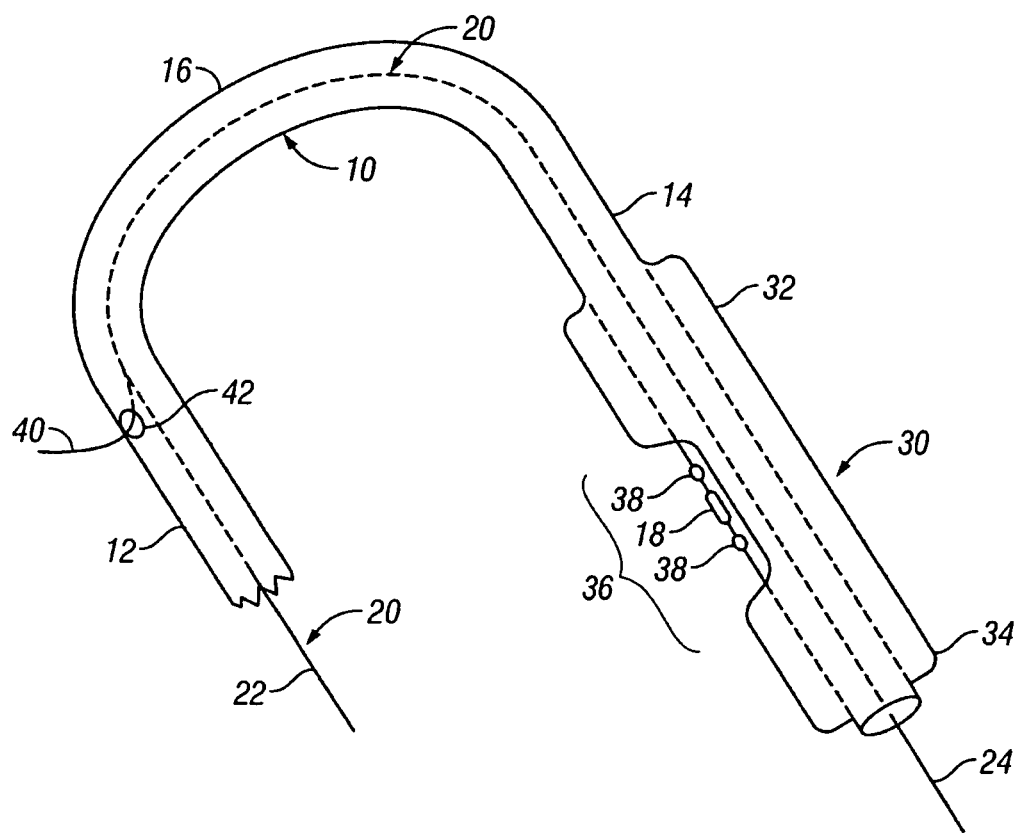
FIG. 1 illustrates an embodiment of a balloon catheter device according the present invention with the balloon inflated.

Referring now to the figures, which are illustrative of multiple embodiments of the present invention only and are not for purposes of limiting the same, FIG. 1 depicts a device in accordance with one embodiment of the present invention. The balloon catheter illustrated in FIG. 1 includes a hollow catheter tube 10 with a proximal end 12 and a distal end 14. Preferably, the proximal end 12 of the catheter tube 10 is rigid torsionally so that it can transmit rotation from its proximal end 12 to its distal end 14 yet flexible enough to bend as necessary to follow the curve of the patient's arteries. It is also preferred that the distal end 14 of the catheter tube 10 is capable of bending so that it can be steered and directed as it is advanced through the patient's arteries. Accordingly, the catheter tube 10 may be made from any standard material suitable for such purposes, such as a suitable silicone, polyurethane or polyethylene. The catheter tube 10 may have any suitable length and preferably has a length of about 160 cm. The catheter tube 10 may have any suitable internal diameter, and preferably has internal diameter of about 0.33 mm (1 French).

A conventional adapter (not illustrated) may be attached to the proximal end 12 of the catheter tube 10 to facilitate attachment of the catheter tube 10 to an inflation/deflation device (not illustrated). The inflation/deflation device may be any suitable device known in the art, and preferably is a syringe. The catheter tube 10 may also include an inflation lumen (not illustrated) extending between the proximal end 12 of the catheter tube 10 and the balloon 30. The inflation lumen delivers fluid to the balloon 30 to inflate the balloon 30.

FIG. 1 further illustrates a device according to the present invention, including a guide-wire 20, with a proximal end 22 and a distal end 24, which may be advanced inside the hollow catheter tube 10. The guide-wire 20 may have any suitable cross-section and preferably has a cross-section of about 0.014 in. The guide-wire 20 may have any suitable length. The present invention may also include a second guide-wire 40, a third guide-wire 200, and a fourth guide-wire 210, each of which may have any suitable length, any suitable cross-section, and preferably has a cross-section of about 0.014 in. Second guide-wire 40 is advanced through opening 42 in the proximal end 12 of the catheter tube 10. Guide-wire 20, second guide-wire 40, third guide-wire 200, and fourth guide-wire 210 need not have identical or substantially identical specifications, so long as each has suitable specifications.

The balloon catheter includes a balloon 30 (illustrated in its inflated configuration in FIG. 1), which has a proximal end 32 and a distal end 34, and which substantially surrounds the distal end 14 of the catheter tube 10. The balloon 30 may be made of any suitable material, such as a flexible polymer (e.g., nylon or polyethylene), and preferably is fabricated from a semi-compliant material that can be upsized to a larger diameter at pressure greater than 10 atmospheres (mm Hg) allowing the balloon 30 to inflate from a collapsed configuration to an expanded configuration and also to deflate after inflation to selectively return to the collapsed configuration. The pressures, however, at which the balloon 30 inflates and deflates may vary in accordance with the particular catheter and balloon design requirements. The balloon 30 may have any suitable length. The balloon 30 may have any suitable diameter and preferably has a diameter between about 3.0 mm and about 4.5 mm. In other embodiments, the balloon 30 may not substantially surround the distal end 14 of the catheter tube 10, but instead may include a hollow shaft (not illustrated), which has a similar interior diameter to the catheter tube 10 and which bonds to the distal end 14 of the catheter tube 10 by adhesive or heat bonding.

FIG. 1 illustrates how the distal end 14 of the catheter tube 10 or hollow shaft includes an opening 18 large enough to accommodate the guide-wire 20. The opening 18 is preferably round, but may be any suitable shape or configuration. The round opening 18 may have any suitable diameter and preferably has a diameter of about 0.4 mm. The distal end 14 of the catheter tube 10 includes at least one metal radio-opaque marker 38 near the opening 18 in the catheter tube 10 or hollow shaft, and preferably includes two metal radio-opaque markers 38 on opposite sides of the opening 18 as illustrated in FIG. 1. The metal can be any suitable metal, such as platinum or gold, and preferably is gold. A doctor can use the metal radio-opaque markers 38 to verify the position of the opening 18 in the catheter tube 10 relative to the opening of the arterial side branch so that they are properly aligned for advancement of the second guide-wire 40 into the side branch as explained further below.

With further reference to FIG. 1, the balloon 30 also includes an opening 36 on one side between the proximal 32 and distal end 34, which can be aligned to expose the opening 18 in the catheter tube 10 or hollow shaft and the metal radio-opaque markers 38. Preferably, the opening 36 is substantially centered between the proximal end 32 and distal end 34. It is also preferred that the opening 36 is rectangular or wedge shaped, but it may be any other suitable shape or configuration. The opening 36 may have any suitable length and preferably has a length of about 3.0 mm. The opening 36 may have any suitable depth and preferably has a depth of about 1.5 mm.

Figure 3:
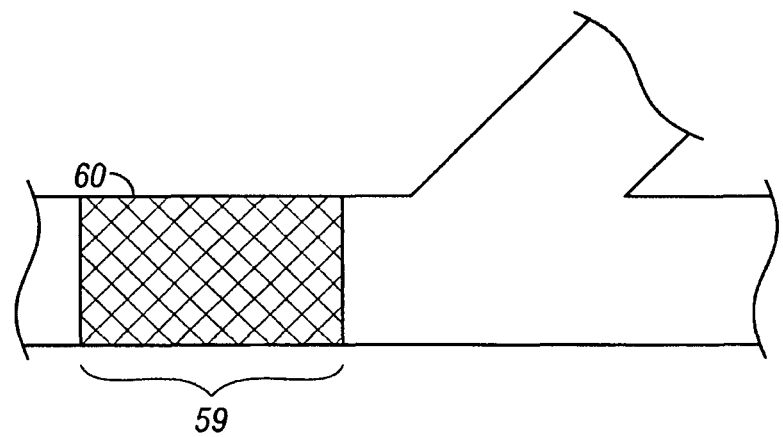
FIG. 3 (prior art) is a side view of a conventional stent device.

As illustrated in FIGS. 2A-C, the device according to the present invention also includes a stent 50. With the exception of the opening 54 and the metal radio-opaque markers 52, as discussed below, the stent 50 of the present invention may have the same or a similar structure as other standard stents known in the industry (e.g., the ACS Multilink stent). For example, as illustrated in FIG. 3 (prior art), a conventional stent in its expanded form may include a multiplicity of longitudinally extending sets of zig-zag struts 60. The stent 50 housing may also be fabricated from any suitable material and by any method known in the art, and preferably is fabricated by laser machining of a cylindrical, thin-walled stainless steel tube.

The stent 50 housing includes an opening on its proximal 56 and distal ends 58, as well as an opening 54 on one side of the housing between the proximal 56 and distal ends 58. The opening 54 may be any suitable shape, but is preferably elliptical so that it can more easily be expanded without fracturing the stent 50. The opening 54 may be any suitable distance from the proximal 56 and distal ends 58 of the stent 50, but is preferably equidistant from the proximal 56 and distal ends 58 of the stent 50. The diameter of the opening 54 may be between about 2.0 mm and about 4.0 mm, and preferably is about 3.0 mm so that it can accommodate the passage of a standard balloon.

In one embodiment, as illustrated in FIGS. 2A-C, the stent 50 housing is cylindrical in shape and is attached to the balloon 30 by any suitable method, but preferably it is crimped on the balloon 30 so that opening 54 is aligned with the opening 36 in the balloon 30. Accordingly, the stent 50 housing is positioned on the balloon 30 so that opening 54 in the stent 50 aligns with the opening 36 in the balloon 30 and the opening 18 in the catheter tube 10, and exposes the catheter tube's 10 metal radio opaque markers 38, allowing the doctor to align the device with the arterial side branch 80 for advancement of a second guide wire 40 that is used to deploy a second stent 110 in the arterial side branch 80.

The stent 50 housing may also include one or more metal radio-opaque markers 52. The one or more radio-opaque markers 52 may facilitate alignment of the opening 54 in the stent 50 with the openings 18 and 36 in the catheter tube 10 and balloon 30, respectively, and the center of the side branch 80. The stent 50 may have any suitable number of metal radio-opaque markers 52, and preferably has three metal radio-opaque markers 52. The metal radio-opaque markers 52 may be any suitable structure and are illustrated as round or semispherical beads. Although the metal radio-opaque markers 52 may be arranged in any suitable pattern, it is generally preferred that the markers 52 are arranged at 90 degree intervals relative to the opening 54 around the circumference of the stent 50 as illustrated in FIGS. 2A-C. Stated differently, it is generally preferred that a metal radio-opaque marker 52 is disposed 180 degrees from the center of opening 54 and that additional metal radio-opaque markers 52 are disposed 90 degrees from the center of opening 54 and 180 degrees from one another. The metal radio-opaque markers 52 may be attached to the stent 50 by any suitable method known in the art, such as welding. The metal can also be any suitable metal, such as platinum or gold, and preferably is gold.

B. Methods of the Present Invention

Figure 4:
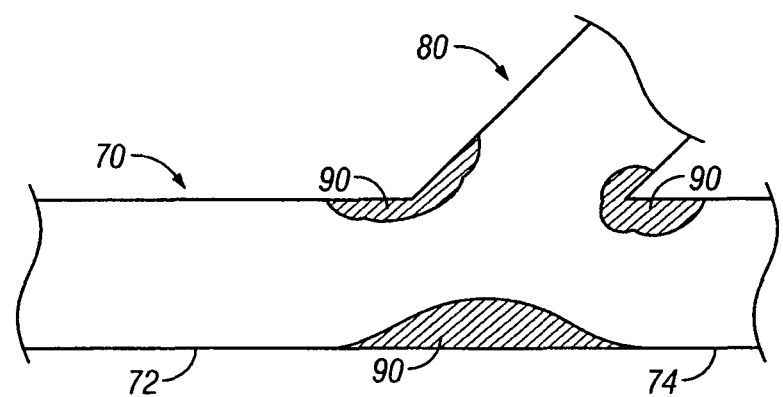
FIG. 4 is a side view of a bifurcated artery.

In addition to the devices described above, the present invention also includes methods of using the devices of the present invention and any other suitable devices in the treatment of bifurcation lesions. As shown in FIG. 4, the illustrated bifurcated artery has a main branch 70 and a side branch 80. The main branch has a proximal portion 72 and a distal portion 74. The artery has plaque buildup 90 starting near the proximal end 72 of the main branch 70 and extending around the bifurcation and into both the side branch 80 and the distal end 74 of the main branch 70.

As an introductory matter, the methods according to the present invention involve accessing the internal volume of an artery of interest. This is generally done by cleaning the insertion area with a sterilized solution, covering it with sterile drapes, numbing it with a local anesthetic, making an incision and inserting a plastic sheath. The insertion area may be any suitable area, but preferably is the femoral artery. In some embodiments, the balloon catheter, which contains the balloon 30 and the stent 50, may then be advanced through the sheath to the bifurcated artery with the plaque buildup. In other embodiments, progressively larger balloons may be used to enlarge the opening before advancing the balloon catheter, which contains the balloon 30 and the stent 50.

Figure 5:
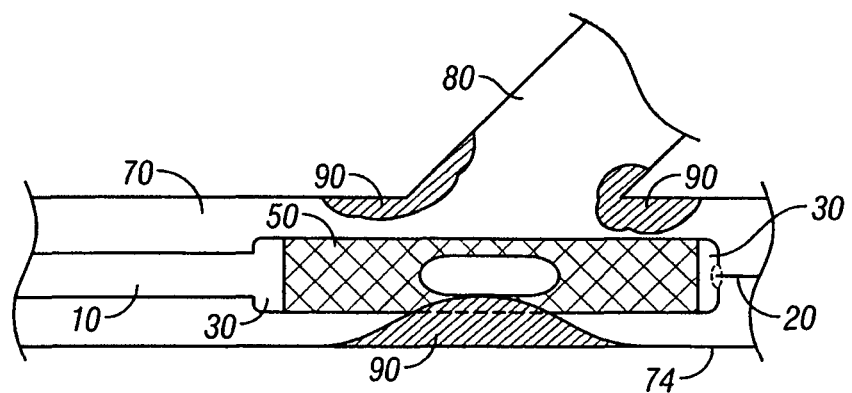
FIG. 5 is a partial cross-sectional view of an embodiment of a device according to the present invention.

As illustrated in FIG. 5, the guide-wire 20 is advanced from the catheter tube 10, down into the main branch 70 and across the plaque buildup 90 so that its distal tip is positioned in the distal segment 74 of the main branch 70. The balloon catheter, which contains the uninflated balloon 30 and the stent 50, is advanced to the site of the plaque buildup 90 in the main branch 70. The balloon 30 and stent 50 are then positioned at the center of the plaque buildup 90 in the main branch 70. Once properly positioned, the balloon 30 is inflated to a suitable pressure, preferably 2-3 atmospheres. Once inflated, balloon 30 can accommodate a second guide-wire 40, which is advanced through the catheter tube 10.

Figure 6:
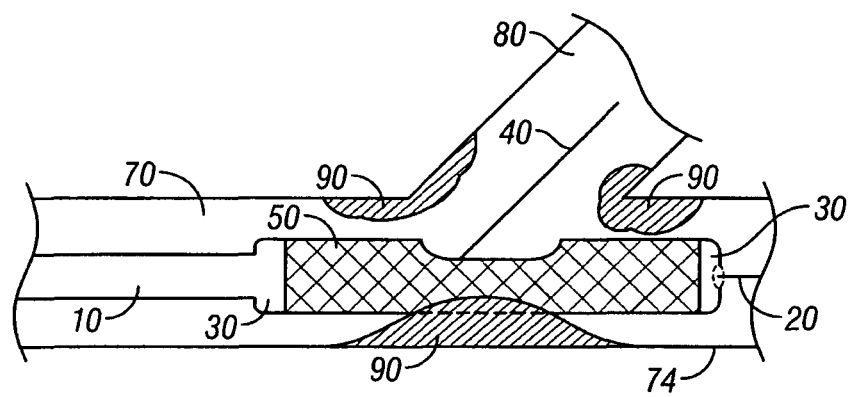
FIG. 6 is a partial cross-sectional view of an embodiment of a device according to the present invention.

The second guide-wire 40 is advanced from the proximal end 12 of catheter tube 10 to a position substantially near the center of balloon 30. FIG. 5 illustrates how, using the metal radio-opaque markers 38 and 52 as a guide, the balloon catheter is torqued to align the openings 18, 36 and 54 in the catheter tube 10, the balloon 30 and the stent 50, respectively, with the opening of the side branch 80. In an embodiment with three metal radio-opaque markers 52, the stent is rotated until the two metal radio-opaque markers 52 that are disposed 90 degrees from opening 54 are positioned such that they appear superimposed when visualized, for example, by fluoroscopy. The stent 50 is then rotated such that the metal radio-opaque marker 52 disposed 180 degrees from opening 54 is lined up directly opposite side-branch 80. This proper alignment permits advancement of the second guide-wire 40 into the side branch 80, as illustrated in FIG. 6. In one embodiment, the second guide-wire 40 is advanced through opening 42 in the proximal end 12 of catheter tube 10. Orthogonal views generated by any method known in the industry can be used to confirm advancement of the second guide-wire 40 into the side branch 80. Preferred methods of visualization include fluoroscopy and cineangiography.

Once the second-guide wire 40 has been advanced into the side branch 80 through the openings 18, 38 and 54 in the catheter tube 10, the balloon 30 and the stent 50, respectively, the balloon 30 is inflated deploying the stent 50. The balloon 30 may be inflated for any suitable amount of time and preferably for about two minutes to press open the blockage and create a channel that increases blood flow through the artery. The balloon 30 may be inflated to any suitable pressure, preferably from about 9 to about 11 atmospheres. The patient may experience chest pain during the procedure because the artery is completely blocked while the balloon 30 is inflated.

In some embodiments, once the stent 50 is deployed, the balloon 30 is deflated and a third guide-wire 200 is advanced outside of the balloon 30 in the main branch 70 and into the side-branch 80. The balloon catheter is withdrawn along with guide-wire 20 and second guide-wire 40, leaving the third guide-wire 200 in the main branch 70 and side branch 80. Using the third guide-wire 200, a second balloon 100 and stent 110 are advanced into the side branch 80 through the previously placed stent 50. The stent 110 may have any suitable diameter and preferably has a diameter of about 3.0 mm. Stent 110 may be similar to, or different than, stent 50. In some embodiments, instead of advancing a third guide-wire 200 into side-branch 80, second guide-wire 40 is not removed and is reused in advancing second balloon 100 and stent 110.

In some embodiments, a fourth guide-wire 210 is then advanced through stent 50 and into the distal portions of main branch 70. A third balloon 120 is then advanced over fourth guide-wire 210 and positioned at the site of the previously deployed stent 50 in the main branch 70. Both the second balloon 100 and the third balloon 120 are deployed substantially simultaneously, in the side branch 80 and the main branch 70, respectfully, preferably using the "kissing balloon" technique as described below. This also serves to deploy the second stent 110 in the side branch 70. In some embodiments, instead of advancing a fourth guide-wire 210 into branch 70, guide-wire 20 is not removed and is reused in advancing third balloon 120.

Figure 7:
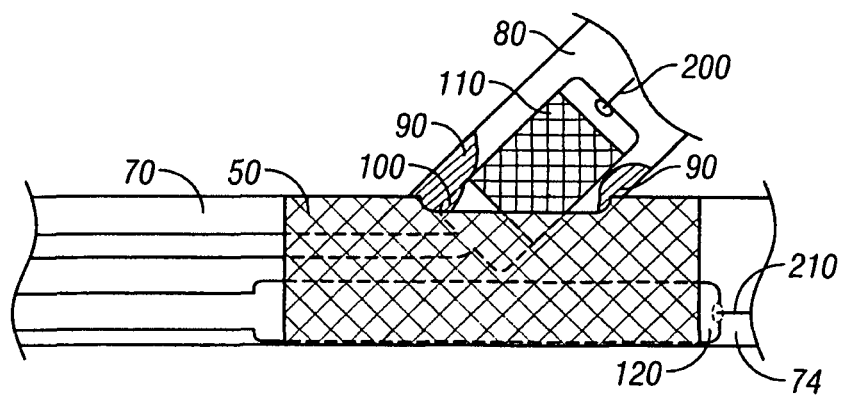
FIG. 7 is a partial cross-sectional view of an embodiment of a device according to the present invention.

FIG. 7 illustrates the kissing balloon technique. The illustrated bifurcated artery has a main branch 70 and a side branch 80. The main branch has a proximal portion 72 and a distal portion 74. The artery has plaque buildup 90 starting near the proximal end 72 of the main branch 70 and extending around the bifurcation and into both the side branch 80 and the distal end 74 of the main branch 70. In the kissing balloon technique illustrated in FIG. 7, a pair of balloon catheters are inserted through the main branch 70 with one of the balloons 100 and 120 being disposed in each of the side branch 80 and the distal end 74 of the main branch 70. The proximal ends of the balloons 100 and 120 typically remain in the main branch 70 and contact or "kiss" each other.

The balloons 100 and 120 are then deflated and removed, while the stents 50 and 110 remain permanently in place to hold the artery open. In some embodiments, the stents 50 and 110 are drug-eluting stents coated with an agent that inhibits restenosis. In one embodiment, the agent is an antibiotic called sirolimus (also called rapamycin), which is slowly released into the artery. Sirolimus is a cytostatic drug, which inhibits cell growth and division, and T-Cell activation and proliferation. T-cells initiate an inflammatory response that commonly follows implantation, and inflammation can lead to restenosis. The agent may be released into the artery for any suitable number days after implantation, and preferably for about 30 days after implantation. Clopedigrol (Plavix®) may also be prescribed for the patient. Clopedigrol is a potent aspirin-like medicine that reduces the risk for development of blood clots inside the stents 50 and 110 during the first few weeks after implantation.

After the procedure, the sheath or sheaths are removed and pressure is applied to the area—usually for five to fifteen minutes—to close off holes in the arteries made by insertion of the sheaths. A gauze dressing is taped to the area and the patient must lie on their back for four to six hours, while normal blood clotting seals the holes in the arteries. Alternatively, holes made in the femoral artery can be sealed immediately after catheterization by stitching them closed or plugging them with collagen. If either of these methods is used, the patient may be able to sit up within an hour of the procedure and begin walking within several hours.

In some embodiments, the above described or other suitable balloon angioplasty procedure may be performed after removal of arterial plaque by atherectomy. The atherectomy may be of any suitable type, and preferably is either laser, rotational, directional or transluminal extraction atherectomy. In laser atherectomy, a laser attached to the tip of a thin flexible catheter emits short pulses of light that ablate plaque. The patient may be injected with tagged antibodies that attach to the plaque and "guide" the laser pulses to the plaque, avoiding damage to the artery walls with the laser beam. Rotational atherectomy, or rotablation, may be used to treat arteries with very long, calcified or solid blockages or arteries with plaque that has regrown inside a stent by using a burr, or surgical drill bit, tipped with very fine diamond chips to pulverize the plaque, which is then suctioned out continuously. Directional atherectomy employs a catheter tipped with a device consisting of a cup-shaped blade and a container. The blade cuts away plaque from the artery and deposits it into the container. When the catheter and device are withdrawn, the plaque is removed from the body. Transluminal extraction atherectomy involves a special catheter tipped with a hollow tube and rotating blades. As the blades cut plaque away from the arterial wall, the debris is suctioned out of the body through the tube.

Thus, it is seen that devices and methods for treating bifurcation lesions are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative embodiments may be implemented to achieve the desired features of the present invention. Also, a multitude of different constituent part names other than those depicted herein may be applied to the various parts of the devices. Additionally, with regard to operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent.

The invention claimed is:

1. A device, comprising:
a balloon catheter for accessing an internal volume of an artery that is divided into a first and second branch, the balloon catheter comprising a first catheter tube, a first balloon and a first stent, the first catheter tube, the first balloon and the first stent each having an opening;
a first guide-wire for advancing the balloon catheter to a site of plaque buildup substantially near the first and second branch, such that the balloon catheter is substantially at the center of the plaque buildup in the first branch;
a second guide-wire that is advanced through the first catheter tube to a position substantially near the center of the first balloon;
at least one metal radio-opaque marker on the balloon catheter that is used as a guide to align the openings in the first catheter tube, the first balloon and the first stent, respectively, with an opening to the second branch;
wherein the second guide-wire is advanced into the second branch through the openings in the first catheter tube, first balloon and first stent;
wherein the first balloon is inflated to deploy the first stent, and then the first balloon is deflated;
a third guide-wire that is advanced into the second branch;
a second balloon catheter that is advanced using the third guide-wire to the second branch through the first stent, the second balloon catheter comprising a second catheter tube, a second balloon and a second stent;
a fourth guide wire that is advanced into the first branch;
a third balloon catheter that is advanced using the fourth guide wire to the site of the previously deployed first stent in the first branch, which comprises a third catheter tube and a third balloon;
wherein when the second and the third balloons are inflated, whereby the second stent is deployed in the second branch; and
wherein the second and third balloons are deflated and removed from the internal volume.

2. The device of claim 1, wherein the at least one metal radio-opaque marker is gold or platinum.

3. The device of claim 1 wherein the first catheter tube has the opening located near a distal end of the first catheter tube and the at least one metal radio-opaque marker is located substantially near the opening in the first catheter tube.

4. The device of claim 1, wherein the at least one metal radio-opaque marker comprises two metal radio-opaque markers and the first catheter tube includes the two metal radio-opaque markers on opposites side of the opening in the first catheter tube.

5. The device of claim 1, wherein the at least one metal radio-opaque marker comprises three metal radio-opaque markers and the first stent includes the three metal radio-opaque markers, which are spaced at approximately 90 degree angles relative to the opening in the first stent.

6. The device of claim 1, wherein the first balloon has proximal and distal ends, and the opening in the first balloon is substantially equidistant from the proximal and distal ends of the first balloon.

7. The device of claim 1, wherein the opening of the first balloon is wedge-shaped.

* * * * *